United States Patent [19]

De Vringer

[11] Patent Number: 5,667,800

[45] Date of Patent: Sep. 16, 1997

[54] TOPICAL PREPARATION CONTAINING A SUSPENSION OF SOLID LIPID PARTICLES

[75] Inventor: Tom De Vringer, Zoetermeer, Netherlands

[73] Assignee: Yamanouchi Europe B.V., Netherlands

[21] Appl. No.: 467,212

[22] Filed: Jun. 6, 1995

Related U.S. Application Data

[62] Division of Ser. No. 131,480, Oct. 4, 1993, abandoned, and a continuation of Ser. No. 857,467, Mar. 25, 1992, abandoned.

[30] Foreign Application Priority Data

Mar. 25, 1995 [EP] European Pat. Off. .............. 91200664

[51] Int. Cl.⁶ .................................................. A61K 9/127
[52] U.S. Cl. ..................... 424/450; 424/78.02; 424/78.03
[58] Field of Search ............................ 424/78.02, 78.03, 424/450

[56] References Cited

U.S. PATENT DOCUMENTS

| | | | |
|---|---|---|---|
| 4,404,228 | 9/1983 | Cloosterman et al. .................. 426/98 |
| 4,880,634 | 11/1989 | Speiser ................................... 424/450 |
| 5,053,217 | 10/1991 | Lehigh .................................... 424/45 |
| 5,174,930 | 12/1992 | Stainmesse et al. ..................... 424/450 |

*Primary Examiner*—Peter F. Kulkosky
*Attorney, Agent, or Firm*—McDonnell Boehnen Hulbert & Berghoff

[57] ABSTRACT

An aqueous suspension of solid lipoid nanoparticles, comprising at least one lipid and preferably also at least one emulsifier, for topical application to the body, is provided. The solid lipoid nanoparticles have a mean particle size of between 50–1000 nm and their concentration is between 0.01–60 wt %, by weight of the suspension. Also topical preparations, comprising said suspension of solid lipoid nanoparticles, are provided. A medicament can be incorporated into the continuous phase of the suspension or in a vehicle, which is added to said suspension.

The invention further provides manufacturing methods for the aqueous suspension of solid lipoid nanoparticles as well as for preparations comprising such suspension.

3 Claims, 3 Drawing Sheets

TOPICAL PREPARATION CONTAINING A SUSPENSION OF SOLID LIPID PARTICLES

This is a divisional of application Ser. No. 08/131,480 filed Oct. 4, 1993 now abandoned and a continuation of 07/857,467 filed Mar. 25, 1992 now abandoned.

The present invention is concerned with a suspension of solid lipid particles and with liquid or semisolid preparations, containing said suspension, for topical application to the body, and with the manufacture thereof.

BACKGROUND OF THE INVENTION

There is a great variety of known liquid or semisolid preparations for topical application to the body, and they are generally based on aqueous or other polar liquids, on liquid or semisolid lipids, or on mixtures thereof. When the preparation is based on a mixture of an aqueous liquid and a lipid substance, the preparation is an emulsion, which may be a water-in-oil (w/o) emulsion in which the lipid substance is the continuous phase, or an oil-in water (o/w) emulsion in which the aqueous liquid is the continuous phase. Each of these types of emulsions is prepared with its own type of emulsifier. EP-B-69423 shows that the type of emulsion is determined by the type of emulsifier used, rather than by the relative concentrations of aqueous or lipid components present. Examples of known emulsions of the w/o type are the ointments, which generally are semisolid. As examples of known emulsions of the o/w type lotions, which are liquid, and creams and gels, which are semisolid, can be mentioned.

The liquid or semisolid lipids, contained in the above-described liquid or semisolid w/o or o/w emulsions, generally are responsible for a cosmetically and medically important effect, viz. occlusion. By occlusion is meant the formation of a "barrier", which causes reduction of water loss through the epidermis, after treatment thereof with such lipid containing emulsions. The occlusive effect is positively correlated to the lipid content of the emulsion. The resulting desirable cosmetic effect of occlusion is emolliency. The resulting desirable medical effect of occlusion is a better penetration into the skin and a better effectiveness of many medicaments, incorporated into an occluding emulsion, after topical application of the same. On the other hand, such lipid containing emulsions have the disadvantage that they are greasy and messy, resulting in a shining appearance of the treated area and in staining of the clothes, and these undesirable properties are also positively correlated to the lipid content of the emulsion.

H. Tsutsumi et al., J. Soc. Cosmet. Chem., 30, 1979, 345–356 described oil-in-water emulsions of different particle size distribution prepared out of water, solid paraffin (melting point 48° C.) and a mixture of polyoxyethylene (20) sorbitan monooleate and sorbitan monooleate. The solid particles of the resulting emulsions had a mean diameter of about 3–65 μm. The occlusivity of the emulsions was found to be inversely proportional to the particle size. However, in the present inventors' experience these types of emulsions, containing solid paraffin particles of micrometer dimensions (microparticles), were found to be inherently unstable. Also, these types of emulsions were found to exert a lower occlusivity as compared with conventional emulsions.

EP-B-167825 discloses a medicament-containing carrier system for peroral use, comprising a 1–20 wt % aqueous suspension of solid lipoid nanopellets with a particle size of 50–1000 nm, the lipoid particles containing 5–70 wt % of lipids, 0.01–70 wt % of an emulsifier and 0.05–25 wt % of the medicament. Due to their small size, the lipoid particles in toto are easily absorbed from the gastro-intestinal tract. Among the advantages of this type of drug-containing carrier system for oral administration an improved bioavailability of those medicaments, which are poorly soluble, poorly absorbed from the digestive tract, chemically or enzymatically inactivated in the digestive tract or prone to the so-called first-pass effect, is to be mentioned in particular.

SUMMARY OF THE INVENTION

The present invention provides, for topical application to the body, a stable aqueous suspension of solid lipoid nanoparticles, comprising at least one lipid and preferably also at least one emulsifier.

Also is provided, for topical application to the body, a preparation which comprises a stable aqueous suspension of solid lipoid nanoparticles, comprising at least one lipid and preferably also at least one emulsifier, and having a mean particle size of between 50 and 1000 nm, and optionally comprising one or more medicaments outside the solid lipoid nanoparticles.

The invention further provides manufacturing methods for said suspension and preparation, comprising the steps of:

a. melting an appropriate quantity of a solid lipid or a mixture of (solid) lipids in a heated aqueous liquid, preferably in the presence of an effective amount of emulsifier(s);

b. vigorously dispersing the molten lipid(s) in the aqueous liquid, in a manner resulting in the formation of molten lipoid droplets of 50–1000 nm;

c. allowing the dispersion to cool until the dispersed lipoid droplets solidify and a suspension of solid lipoid nanoparticles is formed;

d. optionally adding to the suspension, obtained in step c., a pharmaceutically acceptable vehicle; and e. optionally adding to the continuous phase of the suspension or to the pharmaceutically acceptable vehicle a topically effective amount of one or more medicaments.

LEGENDS TO THE FIGURES

DETAILED DESCRIPTION OF THE INVENTION

Figure 1:
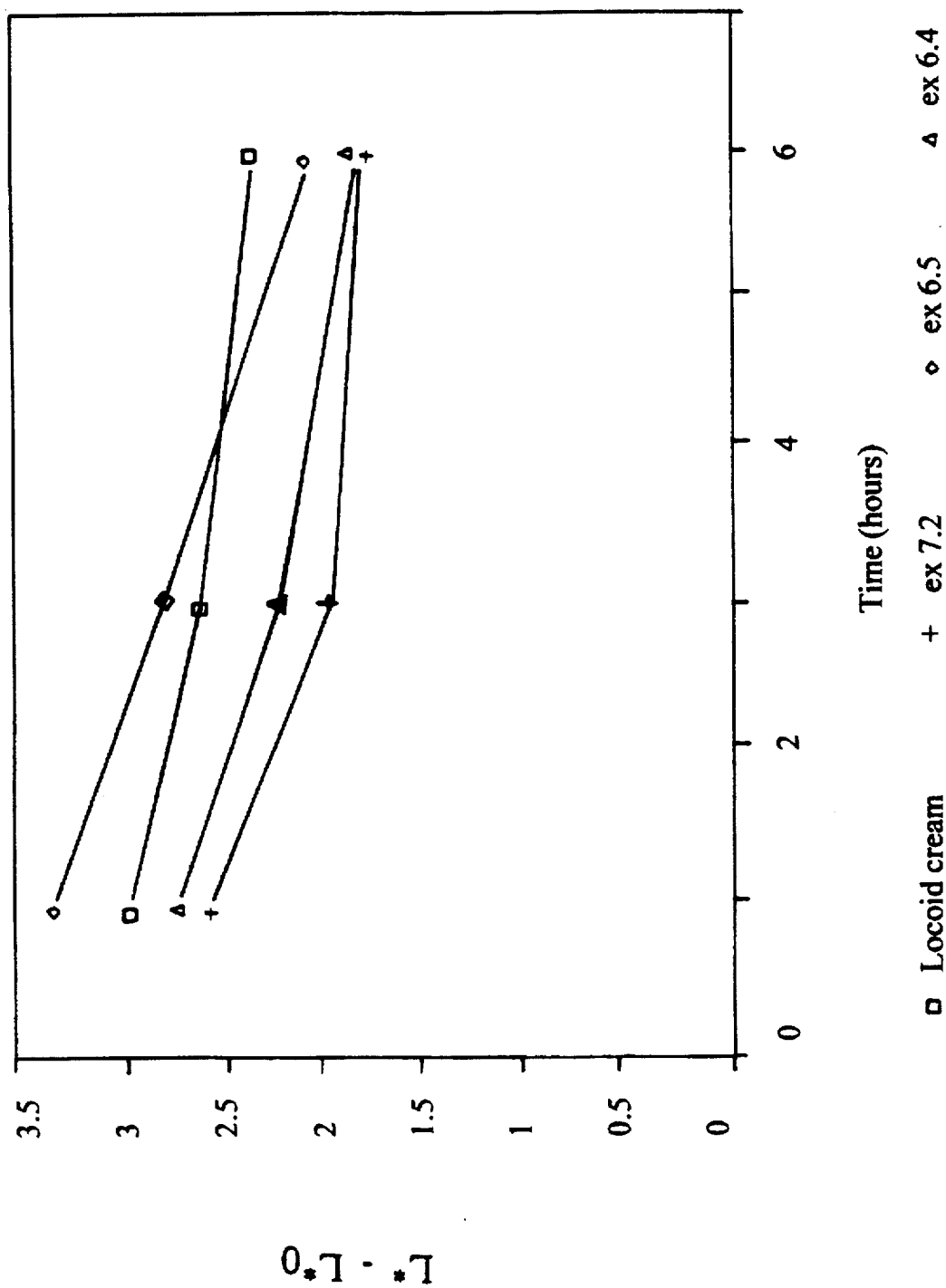
FIG. 1 is a graphical representation of the blanching of the skin as a function of time, after topical application of four hydrocortisone-17α-butyrate containing preparations.

It has now been found that by partially or completely replacing the liquid or semisolid lipid containing emulsion, as generally used in the art, by a suspension of solid lipoid particles having a mean particle size of between 50–1000 nm (nanoparticles), a very stable preparation is made which has maintained the occlusive effect, generally known to be inherent to lipid containing emulsions, while the appreciation with respect to the cosmetic properties of the preparations according to the present invention is greatly improved as compared to that of the lipid containing emulsions known in the art. The novel preparation can be advantageously used for providing emolliency and softness to the skin.

It has further been found that topically effective medicaments can be advantageously incorporated into the continuous phase of the novel suspension of solid lipoid nanoparticles. In addition to known advantages, which are inherent to drug-containing occluding preparations, among which a better penetration into the skin and nails and a better effectiveness of the medicaments incorporated therein are to be mentioned, said novel preparations have also shown other surprising effects: a better regulated drug delivery, especially a sustained release, and a lower irritancy of intrinsically irritant medicaments, incorporated therein.

The invention therefore provides for topical application to the body an aqueous suspension of solid lipoid nanoparticles, comprising at least one lipid and preferably also at least one emulsifying agent.

The invention also provides, for topical application to the body, preparations, comprising said aqueous suspension of solid lipoid nanoparticles.

It will be appreciated that topical application to the body includes the application to the skin, hairs and nails.

The solid lipoid nanoparticles according to the invention have a mean particle size between 50–1000 nm. Preferably, the particle size is between 100–400 nm, more preferably between 150–300 nm.

The concentration of the solid lipoid nanoparticles according to the invention is between 0.01–60%, preferably 5–45%, more preferably 10–30%, by weight based on the weight of the suspension.

The lipoid nanoparticles according to the present invention are solid at room temperature. Therefore, the solid lipids of the nanoparticles according to the invention are those lipids having a melting temperature range between 30°–100° C., preferably between 40°–95° C. When mixtures of lipids are employed, they may partly contain lipids having a melting temperature range lower or higher than between 30° and 100° C., respectively, as long as the complete mixture has a melting temperature range which is within these limits.

The lipoid nanoparticles of the present invention can comprise a single solid lipid or a mixture of (solid) lipids. Suitable solid lipids are for example:

higher saturated alcohols, in particular the aliphatic alcohols having 14–30 carbon atoms, such as cetostearyl alcohol;

waxes, such as carnauba wax;

hydrocarbons, such as solid paraffins (=hard paraffins);

sphingolipids;

synthetic esters, such as cetyl palmitate;

higher fatty acids of 12–30 carbon atoms, such as stearic acid;

and the mono-, di- and triglycerides of higher saturated fatty acids having 10–30 carbon atoms, such as glyceryl trilaurate and hydrogenated castor oil.

A preferred solid lipid according to the invention is solid paraffin, having a melting temperature range of 54°–57° C.

Although there exist solid lipids with which a preparation according to the invention can be made without any emulsifier being added (examples of these are the sphingolipids), in most cases an emulsifier is needed.

It will be appreciated that the nanoparticles, formed from a mixture of lipids and emulsifying agents, still have to be solid at room temperature.

The concentration of emulsifier(s) will vary with the type of the lipids and emulsifiers used and may be from 0.01–20%, preferably 0.1–10%, more preferably 1–5%, by weight based on the weight of the suspension.

A variety of emulsifiers, belonging to both the groups of w/o and o/w emulsifiers and ranging in HLB (Hydrophilic-Lipophilic Balance) number from about 2 to about 80, has been found to be effective for dispersing the molten solid lipid(s) in the heated aqueous liquid. Preferably, the emulsifier has a HLB number of about 8–40. The choice of the emulsifier will depend of the particular solid lipid(s) used.

Examples of suitable emulsifiers are:

the cationic emulsifiers, such as cetyltriethylammonium bromide;

the anionic emulsifiers, such as sodium lauryl sulphate;

the amphoteric emulsifiers, such as hydroxyethyl imidazoline (VARINE®);

block copolymers, such as polyoxyethylenepolyoxypropylene alkyl ethers (e.g. PLURONIC F68®);

non-ionic emulsifiers, such as polyoxyethylene sorbitan fatty acid esters (e.g. TWEEN 20®), polyoxyethylene alkyl ethers (e.g. BRIJ 97® and CETOMACROGOL 1000®), polyoxyethylene fatty acid esters (e.g. MYRJ 52®), sorbitan esters (e.g. SPAN 80®), sucrose esters (e.g. WASAG ESTER 7®);

and further suitable emulsifiers, such as the lecithins, the silicone surfactants, the betains and the polyglycerol fatty acid esters.

Preferably, non-ionic emulsifiers are used. More preferably, the emulsifiers are chosen from the groups of polyoxyethylene alkyl ethers and sorbitan esters.

A mixture of different emulsifiers can also be used advantageously.

The continuous phase of the suspension of solid lipoid nanoparticles according to the present invention preferably comprises water, but may also comprise a mixture of water with non-aqueous, polar liquids, for example alcohols, such as ethyl alcohol, glycerol, propylene glycol, and pyrrolidones, such as N-methyl pyrrolidone and 2-pyrrolidone.

The invention further provides a method for the production of an aqueous suspension of solid lipoid nanoparticles for topical application to the body, comprising the steps of:

a. melting an appropriate quantity of at least one solid lipid (0.01–60% by weight based on the weight of the suspension), and preferably also an effective amount of at least one emulsifier (0.01–20% by weight based on the weight of the suspension) in a heated aqueous liquid, preferably water;

b. vigorously dispersing the molten lipid(s) in the aqueous liquid, in a manner resulting in the formation of molten lipoid droplets having a particle size of between 50 and 1000 nm;

c. allowing the dispersion to cool until the dispersed lipoid droplets solidify and a suspension of solid lipoid nanoparticles is formed.

The vigorous dispersing of the molten lipid(s) in the aqueous liquid is essential for the formation of minute droplets of the molten lipid(s). This may be achieved by any of various methods known in the art, such as the method described in EP-B-167825, which comprises mechanical mixing with a high-speed mixer, optionally followed by ultrasound-treatment. A method, which comprises the use of a high sheer homogenizer valve machine, such as a Manton-Gaulin homogenizer, can also be used. A preferred method is microfluidization. A MICROFLUIDIZER® device, manufactured by Microfluidics Corporation, Newton, Mass., USA, can be advantageously used to achieve any desired droplet micronization within the range of 50–1000 nm. The size of the droplets is further influenced by diverse factors, such as the lipoid material used, the emulsifier(s), the temperature and pressure during treatment and the duration of treatment.

After the minute droplets have been formed as described above, the dispersion is allowed to cool until the lipoid droplets solidify, thereby forming the solid lipoid nanoparticles according to the invention. The cooling can be done actively, according to methods known in the art.

The suspension of solid lipoid nanoparticles in an aqueous liquid thus produced, can be used as such on the skin and it has the above-described attractive cosmetic properties. It can also be used to accommodate a topically effective medicament, with the resulting additional, medically attractive properties as described above. Alternatively, this suspension, with or without the presence of a topically effective medicament, can be further mixed with an appropriate, preferably aqueous, polar liquid, with a liquid or semisolid lipid, or with a mixture thereof which may in its turn be a w/o emulsion such as an ointment, or an o/w emulsion such as a lotion, a cream or a gel. The complete preparation, to be applied to the body, may also contain further pharmaceutical excipients.

Topically effective medicaments which may be used in or with the suspension of solid lipoid nanoparticles according to the invention are for example antibiotics, chemotherapeutic agents, anti-viral agents, non-steroidal anti-inflammatory compounds such as indomethacin, salicylic acid and derivatives thereof, anti-pruritics, tar products, nicotinic acid and derivatives thereof, retinoids, sebum synthesis inhibitors such as the imidazole-ethanol esters of EP-B-124186, wound-healing agents, growth factors, or disinfectants such as hexachlorophene, but preferably anti-mycotics such as oxiconazole nitrate, steroidal anti-inflammatory compounds such as hydrocortisone, hydrocortisone-17α-butyrate, budesonide or triamcinolone acetonide, anti-proliferatives, anti-psoriatics, anti-eczema agents and dithranol are added to the preparations according to the present invention. A combination of two or more topically effective medicaments can also be used.

Non-aqueous, polar liquids, which may be mixed with the suspension of solid lipoid nanoparticles according to the invention, are for example alcohols such as ethyl alcohol, glycerol, propylene glycol, and pyrrolidones such as N-methyl pyrrolidone and 2-pyrrolidone.

Liquid or semisolid lipids which may be mixed, as such or in a w/o or o/w emulsion, with the suspension of solid lipoid nanoparticles according to the invention are for example:

waxes, such as jojoba oil;
mineral oils, such as liquid or soft paraffins;
fatty alcohols, such as oleyl alcohol;
esters, such as isopropyl myristate;
vegetable oils, such as coconut oil;
fatty acids, such as linoleic acid; and
silicone oils.

When a w/o or an o/w emulsion is used, to be mixed with the suspension of solid lipoid nanoparticles according to the invention, it will also contain an appropriate w/o or o/w emulsifier, as known in the art of making such w/o or o/w emulsions.

Pharmaceutical excipients which are commonly used are buffers, preservatives, anti-oxidants, moisturizers, penetration enhancers, UV absorbers, dyes, and fragrances.

The invention also further provides a method of production for the preparations, comprising the aqueous suspension of solid lipoid nanoparticles, for topical application to the body, which comprises the additional step of:

adding to the suspension of solid lipoid nanoparticles an appropriate, preferably aqueous, polar liquid, a gel based on such a liquid, a liquid or semisolid lipid, an o/w emulsion, or a mixture of any of the above, to make a solution, a gel, a w/o emulsion or an o/w emulsion in which the solid lipoid nanoparticles are suspended.

The invention also still further provides a method of production for the preparation, comprising an aqueous suspension of solid lipoid nanoparticles and one or more medicaments outside said nanoparticles, which comprises the additional step of:

adding to the continuous phase of the suspension of solid lipoid nanoparticles, or to the solution, w/o emulsion or o/w emulsion in which the solid lipoid nanoparticles are suspended, a topically effective amount of a medicament and optionally pharmaceutically acceptable excipients.

All publications and patent applications cited in this specification are herein incorporated by reference as if each publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

The following Examples will illustrate the invention. Of the compositions described therein, all percentages quoted are by weight.

EXAMPLE 1

Production of suspensions of solid lipoid particles 1.1. A suspension of solid lipoid microparticles was produced as follows:

300 g of solid paraffin, melting point range 54°–57° C., was heated at 80° C. 50 g of CETOMACROGOL 1000® (HLB=16.1) was dissolved in 650 ml of water at 80° C. The lipid phase was added to the aqueous phase and the dispersion homogenized during 5 minutes with a TURRAX® homogenizer, at 2000 R.P.M., and cooled to ambient temperature. The resulting suspension of solid lipoid microparticles had a particle size of more than 2 μm (measured by light microscopy). It was not stable, separation occurring within 20 hours of standing.

1.2. A suspension of solid lipoid nanoparticles was produced as follows:

300 g of solid paraffin, melting point range 54°–57° C., was heated at 80° C. 50 g of CETOMACROGOL 1000® was dissolved in 650 ml of water at 80° C. The lipid phase was added to the aqueous phase and the dispersion homogenized during 5 minutes with a TURRAX® homogenizer, at 2000 R.P.M. This dispersion was fed to a MICROFLUIDIZER® device (type M-110 T equipped with an interaction chamber $F_{20}Y$ and a back pressure chamber $H_{30}Z$), heated in a water bath at 70° C. and operating at a pressure of 10,000 PSI.

After a single run through the MICROFLUIDIZER® device, the emerging dispersion was cooled to ambient temperature. The resulting suspension of solid lipoid nanoparticles had a mean particle size (measured by dynamic light scattering) of 132 nm, and was very stable: even after 30 months of storage there occurred no separation and no agglomeration of particles.

1.3. Another suspension of solid lipoid nanoparticles was produced in the same way as 1.2., using:

100 g of lauric acid triglyceride (DYNASAN-112®), melting point range 43°–45° C., and 40 g of sodium lauryl sulphate (HLB=40), dissolved in 860 ml of water at 55° C.

After a single run through the MICROFLUIDIZER® device, heated in a water bath at 50° C., the emerging dispersion was cooled to ambient temperature, resulting in a very stable suspension of solid lipoid nanoparticles, having a mean size of 180 nm.

1.4. Yet another suspension of solid lipoid nanoparticles was produced in the same way as 1.2, using:

50 g of glycerylstearate, melting point 56° C., and 950 ml of water at 80° C.

After two runs through the MICROFLUIDIZER® device, heated in a water bath at 70° C., the emerging dispersion was cooled to ambient temperature, resulting in a stable suspension of solid lipoid nanoparticles, having a mean size of 191 nm.

1.5. Yet another suspension of solid lipoid nanoparticles was produced in the same way as 1.2., using:

50 g of solid paraffin, melting point range 54°–57° C., with 10 g of SPAN 85® (HLB=1.8), dissolved in the molten paraffin, and 940 ml of water at 80° C.

After three runs through the MICROFLUIDIZER® device, heated in a water bath at 70° C., the emerging dispersion was cooled to ambient temperature, resulting in a stable suspension of solid lipoid nanoparticles, having a mean size of 118 nm.

1.6. Yet another suspension of solid lipoid nanoparticles was produced in the same way as 1.2., from:

50 g of solid paraffin, melting point range 54°–57° C., with 5 g of PHOSPHOLIPON 90® (a lecithin mixture with min. 90% hydrogenated soja phosphatidylcholine and max. 6% Lysophosphatidylcholine, HLB±80, sold by Nattermann Phospholipid GmbH), dissolved in the molten paraffin, and 945 g of water at 80° C.

After two runs through the MICROFLUIDIZER® device, heated in a water bath at 70° C., the emerging dispersion was cooled to ambient temperature, resulting in a stable suspension of solid lipoid nanoparticles, having a mean size of 428 nm.

1.7. Yet another suspension of solid lipoid nanoparticles was produced in the same way as 1.2., from:

200 g of solid paraffin, melting point range 54°–57° C., and 200 g of TAGAT 02® (polyoxyethylene-glycerylmonooleate), dissolved in 600 g of water.

After a single run through the MICROFLUIDIZER® device, heated in a water bath at 80° C., the emerging dispersion was cooled to ambient temperature, resulting in a very stable suspension of nanoparticles, having a mean size of 140 nm.

EXAMPLE 2

Production of a conventional cream, and of creams containing a suspension of solid lipoid microparticles or a suspension of solid lipoid nanoparticles 2.1. A conventional cream was produced as follows:

52 g of petrolatum, 72 g of cetostearyl alcohol, 88.8 g of propylene glycol and 0.8 g of methyl-p-hydroxybenzoate (NIPAGIN M®) were heated together at 70° C. 16 g of CETOMACROGOL 1000® were dissolved in 176 g of water at 70° C. Both phases were mixed together, concurrently using a stirrer at 200 R.P.M. and a TURRAX® homogenizer at 2000 R.P.M. The dispersion was cooled under reduced pressure to ambient temperature.

2.2. Another conventional cream was produced in the same way as 2.1., from:

26 g of cetostearyl alcohol heated to 70° C. and 4 g of CETOMACROGOL 1000® dissolved in 50 g of water at 70° C. Both phases were mixed together, concurrently using a stirrer at 200 R.P.M. and a TURRAX® homogenizer at 2000 R.P.M. The dispersion was cooled to ambient temperature under reduced pressure.

2.3. A cream containing a suspension of solid lipoid microparticles was produced as follows:

200 g of the suspension according to 1.1. were mixed at 30° C. with 80 g of the cream according to 2.2., using in succession a mixer at 200 R.P.M. and a TURRAX® homogenizer at 2000 R.P.M. The resulting cream had a granular appearance.

2.4. A cream containing a suspension of solid lipoid nanoparticles was produced in the same way as in 2.3., by mixing 200 g of the suspension according to 1.2., with 80 g of the cream according to 2.2..

2.5. Another cream containing a suspension of solid lipoid nanoparticles was produced in the same way as in 2.3., by mixing 200 g of the suspension according to 1.2., to which 2 g of NIPAGIN M® was added, with 200 g of the cream according to 2.1..

2.6. Yet another cream containing a suspension of solid lipoid nanoparticles was produced by mixing 134 g of the suspension according to 1.2., to which 2 g of NIPAGIN M® were added, at 30° C. with 22 g of BRIJ 99®, 22 g of cetyl alcohol and 22 g of propylene glycol, with a stirrer at 200 R.P.M.

EXAMPLE 3

Production of a conventional gel, and a gel containing a suspension of solid lipoid nanoparticles 3.1. A conventional gel was produced by suspending 20 g of CARBOPOL 940® in 980 g of water, adjusted to pH=5.0 with TRIS (tromethamine).

3.2. A gel containing a suspension of solid lipoid nanoparticles was produced by mixing (with a propeller stirrer at 1500 R.P.M.) during 10 minutes 600 g of the suspension according to 1.3. with 400 g of the gel according to 3.1..

3.3. Yet another suspension of solid lipoid nanoparticles was produced in the same way as 1.2., from:

100 g of hydrogenated castor oil (CUTINA HR®), melting point about 85° C., and 40 g of sodium lauryl sulphate, dissolved in 860 ml of water at 85° C.

After a single run through the MICROFLUIDIZER® device, heated in a water bath at 90° C., the emerging dispersion was cooled to ambient temperature, resulting in a stable suspension of solid lipoid nanoparticles having a mean size of 195 nm. After 24 hours of storage this suspension gelated, the gel having good cosmetic properties.

EXAMPLE 4

Production of a lotion, containing a suspension of solid lipoid nanoparticles and a lotion containing solid lipoid nanoparticles and a medicament 4.1. A lotion containing a suspension of solid lipoid nanoparticles was produced as follows:

A clear liquid mixture containing 15 g of isopropylstearate and 15 g of octamethylcyclotetrasiloxane was added to a clear solution containing 119 g of water, 3 g of polyoxyethylene (20) oleylether and 50 g of propylene glycol at 75° C.

At this temperature the mixture was stirred at 200 R.P.M. and was concurrently homogenized using a TURRAX® homogenizer at 2000 R.P.M. The resulting liquid emulsion was cooled to 30° C. whilst the mixture was stirred at 100 R.P.M.

100 g of the suspension according to 1.2. was added to the liquid emulsion at 30° C. and mixed using a stirrer at 100 R.P.M.

A thin liquid lotion containing liquid emulsion droplets and solid lipoid nanoparticles was obtained. The lotion had good cosmetic properties.

4.2. A lotion containing solid lipoid nanoparticles and a medicament was produced as follows:

To the dispersion of 1.2., 5 g of NIPAGIN B® and 10 g of NIPAGIN A® were added. 33.3 g of this preserved dispersion were mixed with 48.35 g of a clear 2.1 wt/vol % aqueous dispersion of hydroxypropylcellulose using a stirrer at 200 R.P.M. 2 g of benzyl alcohol, 0.2 g of a lime fragrance, 15 g of N-acetylcysteine and 1.15 g of oxiconazole nitrate were added to the mixture and mixed at 150 R.P.M. at ambient temperature.

EXAMPLE 5

Production of an ointment, containing a suspension of solid lipoid nanoparticles 5.1. An ointment containing a suspension of solid lipoid nanoparticles was produced as follows:

At 30° C. 25 g of isopropylstearate, 54 g of octamethylcyclotetrasiloxane and 6 g of cetyl dimethicone copolymer were mixed using a stirrer at 300 R.P.M. A clear liquid oily mixture was obtained.

100 g of the suspension according to 1.2. was diluted with an aqueous solution of sodium chloride (1 wt %) to 215 g.

The aqueous suspension of solid lipoid nanoparticles was added to the oily mixture at 30° C., whilst the mixture was concurrently stirred at 200 R.P.M. using a stirrer. The resulting mixture was homogenized using a TURRAX® homogenizer at 2000 R.P.M., whilst the product was concurrently stirred at 100 R.P.M.

In this way an ointment containing solid lipoid nanoparticles and having very good cosmetic properties was obtained.

EXAMPLE 6

Production of creams and ointments, containing a suspension of solid lipoid nanoparticles and a medicament 6.1. 5 mg of dithranol was hand-mixed in a mortar with 5 g of the cream according to 2.5..

6.2. 10 mg of tretinoin was hand-mixed in a mortar with 10 g of the cream according to 2.5..

6.3. 10 mg of dithranol was hand-mixed in a mortar with 10 g of the cream according to 2.6..

6.4. A cream containing solid lipoid nanoparticles and a medicament was produced as follows:

41.2 g of cetostearyl alcohol, 18.5 g of isopropyl myristate and 19.6 g of octamethylcyclotetrasiloxane were heated together at 55° C. 10.3 g of CETOMACROGOL 1000®, 2.4 g of citric acid (1 aq) and 2.3 g of trisodium citrate, were dissolved in 165.6 g of water at 55° C.

Both phases were mixed using a stirrer at 200 R.P.M. The dispersion was cooled under reduced pressure to a temperature of 30° C. To the dispersion of 1.2., 5 g of NIPAGIN B® and 10 g of NIPAGIN P® were added.

146.3 g of the preserved dispersion of 1.2. and 44.2 g of propylene glycol, in which 0.45 g of hydrocortisone-17α-butyrate was dissolved, were mixed with the cooled dispersion with a stirrer at 220 R.P.M. The resulting cream was cooled down to ambient temperature at reduced pressure.

6.5. An ointment containing solid lipoid nanoparticles and a medicament was produced as follows:

6 g of cetyl dimethicone copolyol, 30 g of isopropyl myristate and 50 g of octamethylcyclotetrasiloxane were heated together at 30° C. To the dispersion of 1.2., 5 g of NIPAGIN B® and 10 g of NIPAGIN P® were added. 100 g of the preserved dispersion of 1.2., 1 g of sodium chloride, 2.5 g of citric acid (1 aq) and 2.4 g of trisodium citrate, 0.3 g of hydrocortisone-17α-butyrate and 108.1 g of water were mixed at 30° C. with a magnetic stirrer at 500 R.P.M.

After mixing the aqueous phase was homogenized by sonification. The homogenized aqueous phase was added to the above-described oil phase whilst mixing at 175 R.P.M. using a stirrer. The dispersion was mixed at 200 R.P.M. for 1 hour and 300 R.P.M. for 1½ hour successively. The resulting cream was cooled to ambient temperature at reduced pressure.

EXAMPLE 7

Production of a gel, containing a suspension of solid lipoid nanoparticles and a medicament 7.1. 5 mg of dithranol was hand-mixed in a mortar with 5 g of the gel according to 3.3..

7.2 A gel containing solid lipoid nanoparticles and a medicament was produced as follows To the dispersion of 1.2., 5 g of NIPAGIN B® and 10 g of NIPAGIN P® were added. 100 g of the preserved dispersion of 1.2., 6 g of isopropyl myristate, 1.8 g of citric acid (1 aq), 8.2 g of a 10 wt % solution of sodiumhydroxide and a solution of 0.305 g of hydrocortisone-17α-butyrate in 60 g of propylene glycol were mixed together using a stirrer at 150 R.P.M. and a TURRAX® homogenizer at 2000 R.P.M. 128.1 g of a 5 wt % aqueous dispersion of CARBOPOL 981® was added whilst stirring at 150 R.P.M. at reduced pressure.

EXAMPLE 8

In vitro occlusivity test

The suspensions according to 1.1 and 1.2, and the creams according to 2.2., 2.3. and 2.4., were compared in the following in vitro occlusivity test:

A vessel in the form of a beaker was used. The vessel had a diameter of 5.5 cm and a height of 7 cm, and was designed to receive on top a closing standard laboratory paper filter (TVN, sold by Schut, The Netherlands), surface 23.8 cm$^2$. The test was performed by placing 50 g of distilled water in the vessel, closing the vessel with the paper filter on the upper surface of which 200 mg of the preparation to be tested was evenly distributed, and placing the closed vessel for a period of 72 hours in a stove at 33° C. and 58% RH. All other conditions having been kept equal, the weight loss of water from the vessel (water flux) after 72 hours exclusively depending of the occlusivity of the preparation tested.

The occlusion factor F of the tested preparation was calculated according to the equation:

$$F=100((A-B)/A)$$

wherein A is the water flux through the uncovered filter, and B the water flux through the filter when covered by the tested preparation.

All preparations were tested in triplicate, the maximal deviation between the results of one preparation being 10%. The following Table 1 presents the means of the occlusion factors F found.

TABLE 1

| Preparation | Water content % | Lipid content % | Solid lipoid particle size nm | Occlusion Factor F |
|---|---|---|---|---|
| 1.1. | 65.0 | 30.0 | >2000 | 5.7 |
| 1.2. | 65.0 | 30.0 | 132 | 78.5 |
| 2.2. | 62.5 | 32.5 | — | 73.0 |
| 2.3. | 64.3 | 30.7 | >2000 | 57.0 |
| 2.4. | 64.3 | 30.7 | 132 | 87.0 |

From these results it has appeared, that solid lipoid microparticles are greatly inferior to solid lipoid nanoparticles in their occlusive effect, and that the addition of solid lipoid microparticles to a cream lowers the cream's occlusivity, while the addition of solid lipoid nanoparticles to a cream raises the cream's occlusivity.

EXAMPLE 9

In vivo dithranol irritancy test, on the rabbit skin

The creams containing dithranol according to 6.1. and 6.3., and the gel containing dithranol according to 7.1., were tested for their irritancy in comparison with the PSORIC-REME® product, a commercially available cream of Essex labs, also containing 0.1% of dithranol.

The backs of four rabbits (albino females of the New Zealand White breed) were shaven. On the next day the preparations to be tested were applied once, 8 preparations per back, randomized in an a-select manner. In each application 0.05 ml of the preparation was applied to a skin area of 2×2 cm. 20 and 140 hours after the preparations were applied, the skin irritation was scored by two independent scorers, according to an arbitrary scale running from 0 to 4 (0 means no erythema, 4 means severe erythema).

Table 2 presents the mean irritancy scores.

TABLE 2

| Preparation | Skin irritancy Score after application at 20 hours | at 140 hours |
|---|---|---|
| 6.1. | 1.0 | 0.5 |
| 6.3. | 1.7 | 1.3 |
| 7.1. | 0.5 | 0.6 |
| PSORICREME ® | 2.4 | 3.4 |

From these results it has appeared, that the preparations according to the invention are much less irritating to the skin than a conventional preparation containing the same amount of an irritating medicament.

EXAMPLE 10

In vivo dithranol anti-proliferative activity test, on the mouse skin

The creams containing dithranol according to 6.1. and 6.3., and the gel containing dithranol according to 7.1., were tested for their activity in comparison with the PSORIC-REME® product, a commercially available cream of Essex labs, also containing 0.1% of dithranol.

The reduction of the uptake of thymidine in the DNA of the epidermis was used as a measure of the anti-proliferative activity of dithranol.

Groups of 10 hairless mice (Hr/hr; Bommice; females) were used. The tested formulations were applied in a quantity of 25 µl to an area of 2×2 cm of their skin, which was compared to 2×2 cm of untreated skin (control). One hour after application the mice received a subcutaneous injection of 25 µl, containing 25 µCi $^3$H-thymidine (Amersham). Three hours after application the mice were killed, their treated and untreated 2×2 cm skin areas prepared, and their epidermis separated by incubation in 2M potassium bromide. Subsequently, the amount of radioactive thymidine, taken up in the DNA of the epidermis in two hours, was measured by using a scintillation counter (TRI-CARB®, Packard).

Table 3 presents the means and standard deviations of thymidine uptake in the treated areas, as percentages of the untreated control areas.

TABLE 3

| Preparation | Thymidine uptake, % of controls | |
|---|---|---|
| | Mean | St. deviation |
| 6.1. | 45 | 14 |
| 6.3. | 42 | 15 |
| 7.1. | 47 | 18 |
| PSORICREME ® | 39 | 15 |

From these results it has appeared, that the anti-proliferative activity of the four tested dithranol formulations is of the same order.

EXAMPLE 11

A combination of a blanching and cosmetic test in vivo on humans

Preparations 6.4., 6.5., 7.2. and LOCOID® cream (0.1 wt % hydrocortisone-17α-butyrate; Brocades Pharma B.V., the Netherlands) containing 23, 20, 12 and 28.1 wt % of non-volatile occlusive lipids, respectively, were tested in a McKenzie-Stoughton vasoconstriction test and a cosmetic test.

11.1. McKenzie-Stoughton vasoconstriction test

The in vivo skin blanching effects of the preparations according to 6.4., 6.5., 7.2. and LOCOID® cream were compared in a McKenzie-Stoughton vasoconstriction test.

The test was conducted on a panel of non-patient volunteers (1 female and 7 males). Sites were marked on the flexor aspect of both fore-arms by light indentation with a circular punch of 15 mm diameter. Sites were at least 4 cm distant from wrist and elbow. The precoded preparations were applied to these sites according to a Latin square experimental design. Preparations were applied by technicians, in amounts of 10 µl per site using a Hamilton injection syringe (Gastight 1710) fitted with a 18 gauge blunt needle. The application sites were then covered, but not occluded with a guard, which was held in place with a ring of surgical tape (diameter: external 50/60 mm, internal 25 mm). Dressings were removed and arms were Washed with soap and lukewarm water 17 hours after application of the formulations. Accordingly, blanching at the various sites was assessed by determining the change in the luminescence parameter L* of the treated skin as compared to the untreated skin (L*$_0$), using a MINOLTA CHROMAMETER C300®. This was done at 1, 3 and 6 hours after removal of the preparations. The experiment was conducted in a double blind fashion.

The results of this study (see FIG. 1) showed that there was no statistical significant difference between the four preparations tested.

11.2. Cosmetic acceptability test

For performing the cosmetic acceptability test preparations were prepared in accordance with 6.4., 6.5. and 7.2. but without adding hydrocortisone-17α-butyrate. As references LOCOID® cream base (without hydrocortisone-17α-butyrate) and the highly appreciated cosmetic non-ionic liposomal cream CANDERMYL® (Alcon, Galderma, France) were used. All preparations were coloured with a small amount of the yellow colorant E102 and were perfumed with a small amount of a lavender fragrance.

The preparations were compared in 20 non-patient volunteers in a left-right cosmetic acceptability study. Every volunteer participated three times in a double blind manner. 50 μl of the precoded preparations were applied on the flexor aspect of both forearms by a technician. The volunteer had to answer questions about the appearance, spreading properties, stickiness, skin-feel of the preparations and finally the volunteer was asked to rank the preparations with respect to his/her preference. In total 60 preferences were given. The results are presented in Table 4.

TABLE 4

| Preparation | Number of preferences |
|---|---|
| 6.4. | 14 |
| 6.5. | 16 |
| 7.2. | 15 |
| LOCOID ® cream base | 7 |
| CANDERMYL ® cream | 8 |

From the results presented in Table 4, it has appeared that the three solid lipoid nanoparticles containing preparations are cosmetically superior over the two reference preparations.

Considering the results of both the McKenzie-Stoughton vasoconstriction test and the cosmetic acceptability test it has appeared that the effectiveness of the medicament remains the same whilst the appreciation of the cosmetic properties is increased when non-volatile occlusive lipids in a topical formulation are replaced by a suspension of solid lipoid nanoparticles, according to the invention.

EXAMPLE 12

In vitro nail penetration using lotions, containing solid lipoid nanoparticles and oxiconazole nitrate, and lotions containing N-acetylcysteine and oxiconazole The lotion of 4.2. and as a reference a clear solution containing 1.5 g of N-acetylcysteine, 0.115 g of oxiconazole nitrate, 0.02 g of a lime fragrance and 0.0375 g of hydroxypropylcellulose in a vehicle consisting of 0.2 g of benzyl alcohol, 0.33 g of water and 6.52 g of ethanol, were tested for the ability of oxiconazole to penetrate into a pig's nail. To both preparations 1 μCi $^{14}$C-oxiconazole per 30 μl preparation was added.

From a pig's nail 8 mm discs were punched. Two times a day (for 7 days) 2 μl of the preparations were applied after cleaning twice the application area with 15 μl of demineralized water and 15 μl of dehydrated alcohol. After 7 days of application 3 mm discs were punched from the application area, the discs were sliced into slices of 50 μm.

The amount of labelled oxiconazole in the slices was determined using a scintillation counter. The determined amount of labelled oxiconazole was used to calculate the total amount of oxiconazole within the slice.

Figure 2:
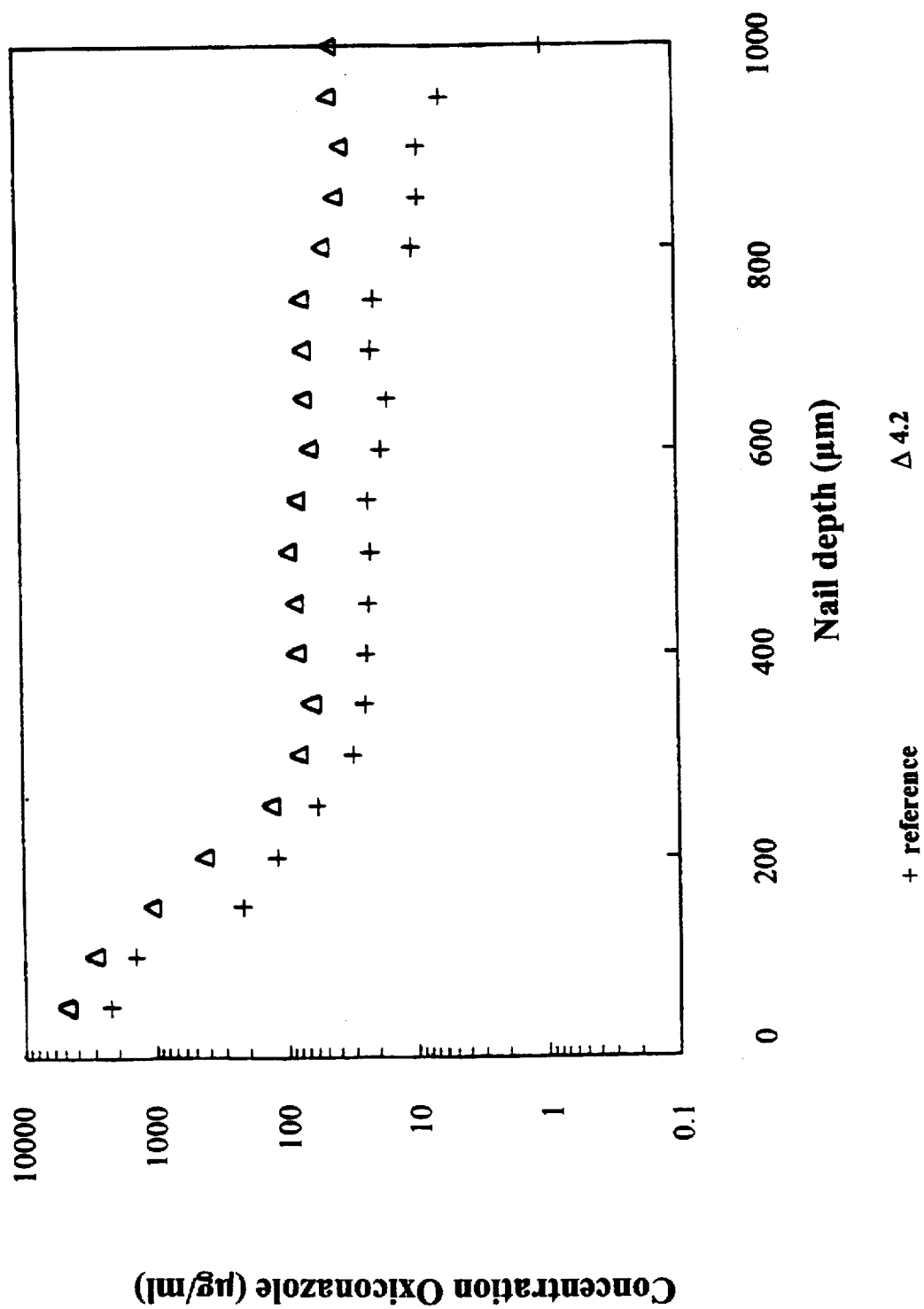
FIG. 2 is a graphical representation of the mean oxiconazole concentrations as a function of the penetration depth into pig's nail, after topical application of two oxiconazole nitrate containing preparations.
Figure 3:
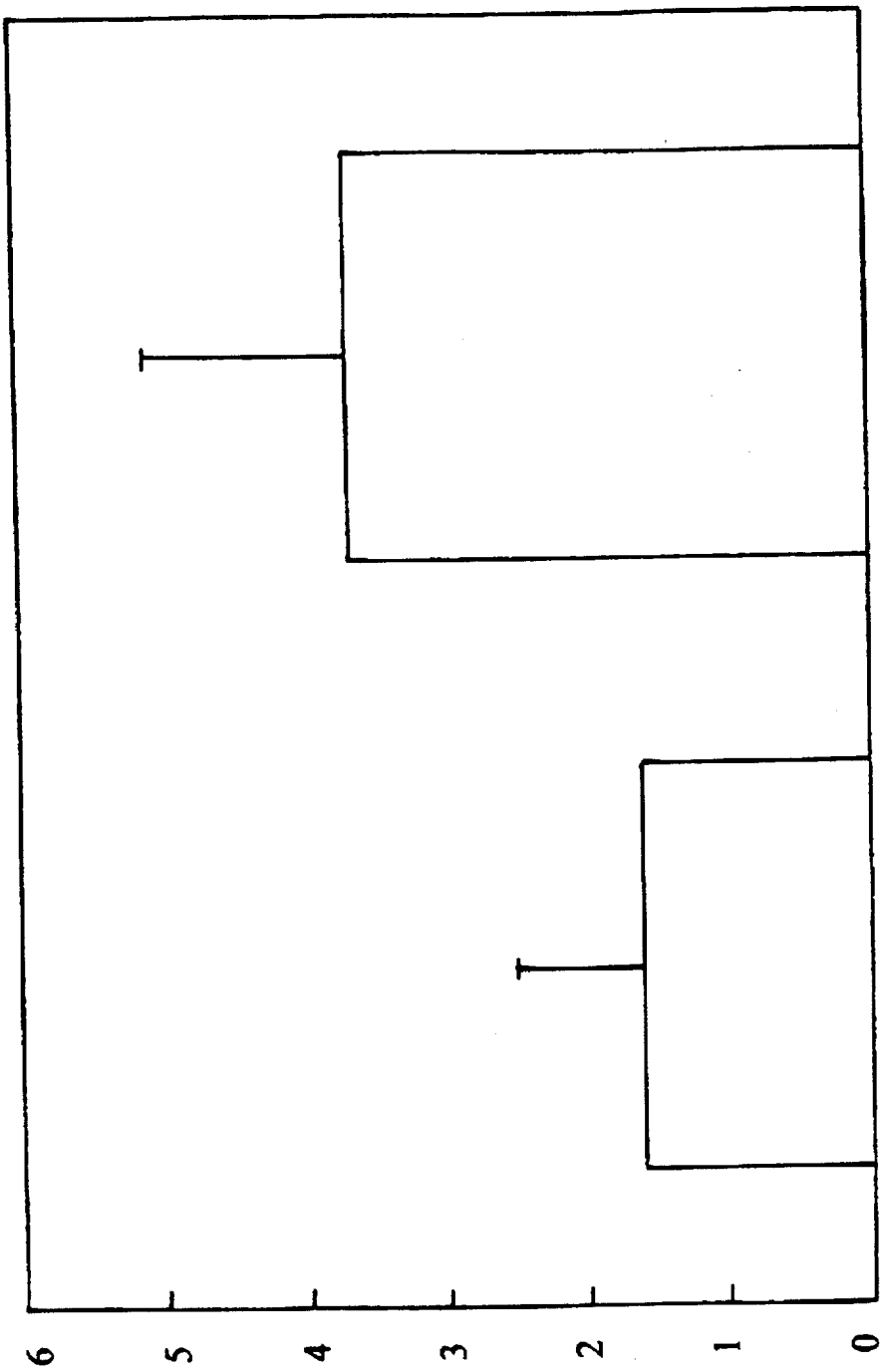
FIG. 3 is a graphical representation of the total amounts of oxiconazole, penetrated into pig's nail, after topical application of two oxiconazole nitrate containing preparations.

The amount of oxiconazole per slice and the total amount of oxiconazole penetrated are graphically represented in FIGS. 2 and 3, respectively.

From FIGS. 2 and 3 it has appeared that the solid lipoid nanoparticles containing preparation causes an increase of the oxiconazole concentration per nail slice and per whole nail, respectively, with respect to the preparation containing N-acetylcysteine and oxiconazole nitrate.

I claim:

1. A composition comprising a lotion, gel, cream or ointment for topical application to the skin, hair, and nails further comprising an aqueous suspension of solid lipoid non-vesicular nanoparticles having a mean particle size of between 50 and 1000 m, the nanoparticles being present in the suspension in a concentration of between 0.01 and 60 wt %, said nanoparticles comprising a mixture of at least one lipid and at least one emulsifier, wherein the lipid is a hard paraffin, wherein said lipid nanoparticles raise the occlusivity of a cream when added thereto.

2. The suspension according to claim 1, wherein the hard paraffin has a melting temperature range of 54° C. to 57° C.

3. The suspension according to claim 1, wherein the solid nanoparticles contain no medicament.

* * * * *